(12) United States Patent
Bradley

(10) Patent No.: US 7,487,791 B1
(45) Date of Patent: Feb. 10, 2009

(54) APPARATUS TO CONTAIN EXCESSIVE LENGTHS OF MEDICAL TUBING AND CABLING

(76) Inventor: Patricia Bradley, 5747 Feezor Rd., Farmington, MO (US) 63640

( * ) Notice: Subject to any disclaimer, the term of this patent is extended or adjusted under 35 U.S.C. 154(b) by 128 days.

(21) Appl. No.: 11/488,294

(22) Filed: Jul. 18, 2006

(51) Int. Cl.
*B65H 75/36* (2006.01)
(52) U.S. Cl. .............................. 137/355.16; 137/355.28
(58) Field of Classification Search ............ 137/355.16, 137/355.28
See application file for complete search history.

(56) References Cited

U.S. PATENT DOCUMENTS

| | | | |
|---|---|---|---|
| 3,514,171 A | | 5/1970 | McGaha |
| 3,556,455 A | * | 1/1971 | Storm et al. ........... 137/355.16 |
| 4,733,840 A | * | 3/1988 | D'Amore .................. 248/205.3 |
| 5,149,017 A | * | 9/1992 | McEntire et al. ........ 244/114 R |
| 5,389,082 A | * | 2/1995 | Baugues et al. ............. 604/174 |
| 5,392,808 A | | 2/1995 | Pierce |
| 5,556,059 A | * | 9/1996 | Maeda et al. ................. 248/49 |
| 5,826,608 A | | 10/1998 | Pierce |
| 5,975,120 A | | 11/1999 | Novosel |
| 6,065,490 A | | 5/2000 | Falcone, Jr. |
| 6,484,959 B1 | | 11/2002 | Grammenz |
| 6,591,858 B2 | | 7/2003 | Peterson |
| 7,166,217 B2 | * | 1/2007 | Holmes et al. ........... 210/257.1 |
| 7,254,850 B2 | * | 8/2007 | Newkirk et al. ........ 137/355.16 |

* cited by examiner

*Primary Examiner*—Kevin L Lee
(74) *Attorney, Agent, or Firm*—Robert C. Montgomery

(57) ABSTRACT

An apparatus to aid in the holding and retention of tubing or cables used on patients in a hospital environment is disclosed. The invention is envisioned to be used on intravenous tubing, air tubing, sensor cables and the like. The invention would comprise a clamshell-like case with the approximate dimensions of two inches high, three inches wide and approximately eight inches long. When opened, a series of "S"-shaped grooves along with one that is straight and routed through the center of the case along the long dimension is visible. Excess tubing or cables are routed back and forth along the "S"-shaped grooves and then out the straight one when the slack is taken in. The case is then snapped shut. The case would be made of a semi-pliable material in lieu of a hard plastic for increased patient comfort should the patient physically contact the invention. The invention can be snapped together in a gang fashion in those instances where more than one cable or tube needs to be controlled. Finally, the invention utilizes an elastic strap to help hold the invention in place. The use of the present invention allows patients connected to medical equipment by cables or by tubing, the ability to move about without becoming entangled or trapped.

18 Claims, 5 Drawing Sheets

APPARATUS TO CONTAIN EXCESSIVE LENGTHS OF MEDICAL TUBING AND CABLING

FIELD OF THE INVENTION

The present invention relates to apparatus to contain excessive lengths of medical tubing and cabling.

BACKGROUND OF THE INVENTION

Hospitals and care facilities use a variety of mechanisms for providing treatment to patients. More particularly, intravenous tubes, sensor cables, and other linear based care mechanisms have been widely used for administering blood, glucose, drugs, oxygen, and the like, to treat patients.

In a familiar hospital environment, most of the patient can be seen connected with numerous linear based care mechanisms, for example, intravenous tubes and sensor cables. Patients connected with such large number of intravenous tubes and sensor cables, is often seen constantly fighting with the intravenous tubes and sensor cables to prevent it from becoming tangled or trapped when they move. Such patients need more care and attention due to the complexity associated with the handling of the large number of tubes and/or cables. The large number and excessive length of tubes results in forming a web of tubes. The web may cause in twisting, tangling, blocking or removing of intravenous tubes or cables that are in use. Such conditions may be risky and dangerous for patients, further jeopardizing their health and welfare, and particularly for those patients who are in intensive care unit. Additionally, such tangling and trapping of tubes and cables may also prove to be uncomfortable, and waste of time for care providers, treating or taking care of patients.

Several approaches have been attempted in the past in the field of devices for storing medical tubes or cables. U.S. Pat. No. 5,392,808 discloses a retractable tubing reel device utilized in conjunction with a oxygen supply tank and nasal oxygen catheter, the device having an extended length of tubing allowing a patient greater movement beyond the immediate area of the oxygen tank, the device having a mechanism for retracting any excess extended tubing thereby preventing constriction and tangling of the tubing. The device retracting the tubing into housing where the tubing is rewound in a manner which also prevents constriction and tangling of the tubing inside the housing. One problem identified with the retractable tubing reel disclosed therein is that the device is limited to use a fixed diameter of cable or tube i.e., nasal catheter. Further, the device is configurationally complex, and more expensive due to the complexity of the mechanism associated with the device.

U.S. Pat. No. 6,591,858 discloses a gas tubing reel includes a housing having a tubing-reel rotatably positioned therein for unwinding and retracting tubing. The tubing-reel is biased in a retracting direction and includes ratcheting and releasing means for selectably paying out or retracting the tubing. One side wall of the housing defines an opening through which the tubing-reel may be slidably removed. The cable reel includes a line guide engaged with a worm gear for reciprocative movement between side walls of the housing whereby to evenly distribute the gas tubing on the tubing-reel. A swivel housing is coupled to the tubing-reel in a bearing relationship and includes an inlet port for receiving an end of the tubing and an outlet port for coupling to a nasal cannula. One disadvantage associated with the disclosed device is that it is limited to the use in providing care to patients undergoing gas therapy. Further, the gas tubing reel disclosed therein is heavy and needs costly maintenance due to the complex mechanical assembly associated with the working of the device.

Accordingly, there remains a need for a portable, economic, and simple to use device that can contain the excessive lengths of medical tubes or cables used in the treatment of patients, while avoiding the problem of twisting, tangling, and blocking of medical tubes and cables connected to patients.

SUMMARY OF THE INVENTION

In view of the foregoing disadvantages inherent in the prior arts, the general purpose of the present invention is to provide an apparatus to contain excessive lengths of medical tubing and cabling, configured to include all the advantages of the prior arts, and to overcome the drawbacks of the prior arts.

In one aspect, the present invention provides an apparatus for containing excessive lengths of linear based care mechanism. The apparatus comprises: a lower base assembly having an entrance opening, an exit opening, and a plurality of grooves forming a captive path, the captive path leading from the entrance opening to meet the exit opening, such that, the captive path receives and contains the excessive lengths of linear based care mechanism; and a captive cover hinged at one end portion to the lower base assembly, such that, the captive cover is capable of covering the excessive lengths of linear based care mechanism, contained in the captive path of the lower base assembly.

In another aspect, the present invention provides an apparatus for containing excessive lengths of linear based care mechanism. The apparatus comprises: a lower base assembly having an entrance opening disposed at a top of the lower base assembly, an exit opening disposed at a bottom of the lower base assembly, and a plurality of grooves forming a straight captive path and an "S" shaped captive path, arranged in a manner, such that, a combination of the straight captive path and the "S"-shaped captive path is capable of receiving and containing the excessive lengths of the linear based care mechanism; a captive cover hinged at one end portion to the lower base assembly, the captive cover having a clasp capable of engaging to a clasp engagement means disposed on the lower base assembly, such that, the captive cover is capable of covering the excessive lengths of linear based care mechanism, contained in the combination of the straight captive path and the "S"-shaped captive path of the lower base assembly.

In yet another aspect, the present invention provides a method of using an apparatus for containing excessive lengths of linear based care mechanism having a lower base assembly, and a captive cover hinged to the lower base assembly. The method comprises: inserting the linear based care mechanism at an entrance opening of the lower assembly; routing the linear based care mechanism downwardly towards a straight captive path of the lower base assembly, and further along an "S"-shaped captive path of the lower base assembly towards a plurality of intersection points of the straight captive path and "S"-shaped captive path until the linear based mechanism reaches a predetermined intersection point of the plurality of intersection points whereupon the linear based care mechanism changes direction and routed along the straight captive path and out of an exit opening of the lower base assembly, and closing the captive cover by engaging a clasp of the captive cover with a clasp engagement means of the lower base assembly, thereby ensuring the linear based care mechanism remaining captive therewithin.

These together with other aspects of the present invention, along with the various features of novelty that characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there are illustrated exemplary embodiments of the present invention.

DESCRIPTION OF THE DRAWINGS

The advantages and features of the present invention will become better understood with reference to the following more detailed description and claims taken in conjunction with the accompanying drawings, wherein, like elements are identified with like symbols, and in which:

DESCRIPTIVE KEY

| | |
|---|---|
| 10 | apparatus to contain excessive lengths of medical tubing and cabling |
| 15 | patient |
| 20 | hospital bed |
| 25 | intravenous pump |
| 30 | intravenous bag |
| 35 | intravenous support stand |
| 45 | elastic strap |
| 50 | fastening means |
| 55 | bed rail support |
| 60 | patient arm |
| 65 | label writing area |
| 70 | lower base assembly |
| 75 | captive cover |
| 80 | clasp engagement means |
| 85 | clasp |
| 90 | multiple arrangement connection appendages |
| 95 | multiple arrangement connection receptacles |
| 100 | straight captive path |
| 105 | "S"- shaped captive path |
| 110 | entrance opening |
| 115 | first intersection point |
| 120 | "U"- shaped captive path segment |
| 125 | second intersection point |
| 130 | "nth" intersection point |
| 135 | exit opening |
| 140 | sidewall structure |
| 145 | right side nub appendage |
| 150 | left side nub appendage |
| 155 | first multi-ganged arrangement module |
| 160 | second multi-ganged arrangement module |
| 165 | oxygen line |
| 170 | third multi-ganged arrangement module |
| 175 | electrical monitoring cable |

DETAILED DESCRIPTION OF THE INVENTION

The best mode for carrying out the invention is presented in terms of its preferred embodiment, herein depicted within FIGS. 1 through 5.

DETAILED DESCRIPTION OF THE FIGURES

Figure 1:
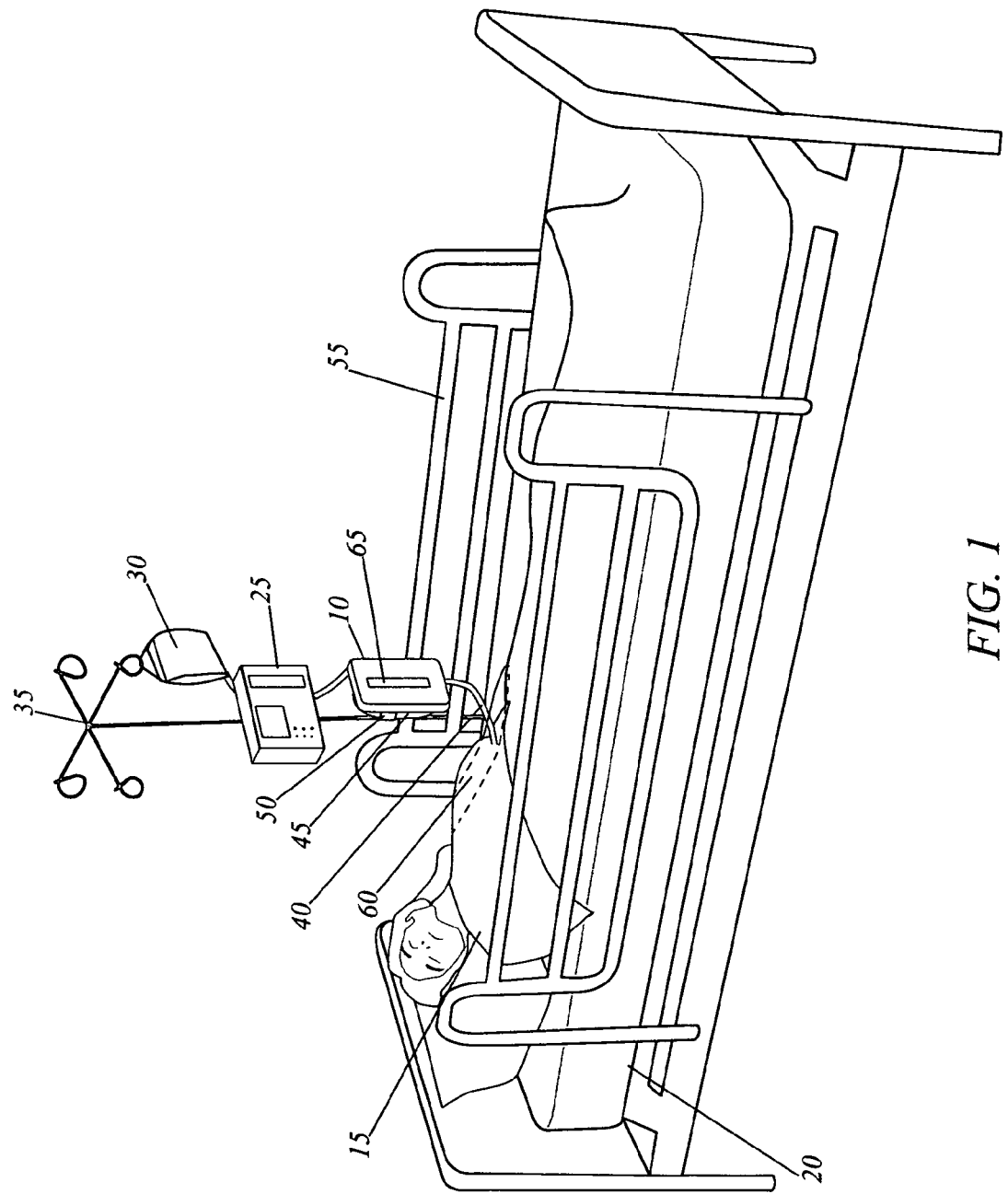
FIG. 1 is a pictorial representation of the apparatus to contain excessive lengths of medical tubing and cabling 10 shown in actual use, according to the preferred embodiment of the present invention; and, FIG. 2 is a front view of the apparatus to contain excessive lengths of medical tubing and cabling 10 shown in an open and unutilized state; and, FIG. 3 is a front view of the apparatus to contain excessive lengths of medical tubing and cabling 10 shown in an open and utilized state; and, FIG. 4 is a sectional view of the apparatus to contain excessive lengths of medical tubing and cabling 10 taken along a line I-I as seen in FIG. 3 with the captive cover 75 in a closed position; and, FIG. 5 is an isometric view of the apparatus to contain excessive lengths of medical tubing and cabling 10 shown in a multi-ganged arrangement.

Referring now to FIG. 1, a pictorial representation of the apparatus to contain excessive lengths of medical tubing and cabling 10 shown in actual use, according to the preferred embodiment of the present invention is disclosed. The apparatus to contain excessive lengths of medical tubing and cabling 10 is shown in use on a patient 15 confined to a hospital bed 20. Said apparatus to contain excessive lengths of medical tubing and cabling 10 is used to contain excess tubing exiting from an intravenous pump 25 and/or an intravenous bag 30, typically contained on an intravenous support stand 35. Said depicted environment is typical for areas such as hospitals, nursing homes and the like, where excess tubing is left hanging on the patient 15, the hospital bed 20, the floor and the like, where it becomes a tripping hazard, or becomes prone to becoming caught on other objects, possibly risking damage or possible disconnection. While FIG. 1 depicts usage in a hospital bed 20 environment, it should be noted that other applications such as at-home care, out-patient care areas, emergency triage care and the like can also experience the beneficial use of the apparatus to contain excessive lengths of medical tubing and cabling 10, and as such, should not be interpreted as a limiting factor of the present invention. Additionally, while FIG. 1 depicts usage of the apparatus to contain excessive lengths of medical tubing and cabling 10 with intravenous tubing 40, other linear type objects such as vacuum lines, feeding tubes, drain lines, electrical monitoring cables, and the like can also be used with the apparatus to contain excessive lengths of medical tubing and cabling 10, and as such, should not be interpreted as a limiting factor of the present invention. The rear of the apparatus to contain excessive lengths of medical tubing and cabling 10 is provided with an elastic strap 45 which is secured with a fastening means 50 such as a snap, or hook and loop fastener to allow attachment of the apparatus to contain excessive lengths of medical tubing and cabling 10 to a local support such as a bed rail support 55. It is also envisioned that the apparatus to contain excessive lengths of medical tubing and cabling 10 could be secured to and around a patient arm 60 which would be especially advantageous in those instances where the patient 15 is mobile to prevent excessive intravenous tubing 40 from dragging on the ground or risking become snagged. Finally, a label writing area 65 is provided on the front of the apparatus to contain excessive lengths of medical tubing and cabling 10 to allow nurses, doctors, or care providers to indicate the functionality of the contained intravenous tubing 40, or other linear based care mechanism. Said labeling will allow care providers to quickly locate necessary intravenous tubing 40 or other linear based patient care mechanism for future care, maintenance and/or removal. Envisioned information to be provided on the label writing area 65 include IV functionality, dosage, time placed, patient information, allergies, and the like. Further description and actual installation and usage of the apparatus to contain excessive lengths of medical tubing and cabling 10 will be provided herein below.

Figure 2:
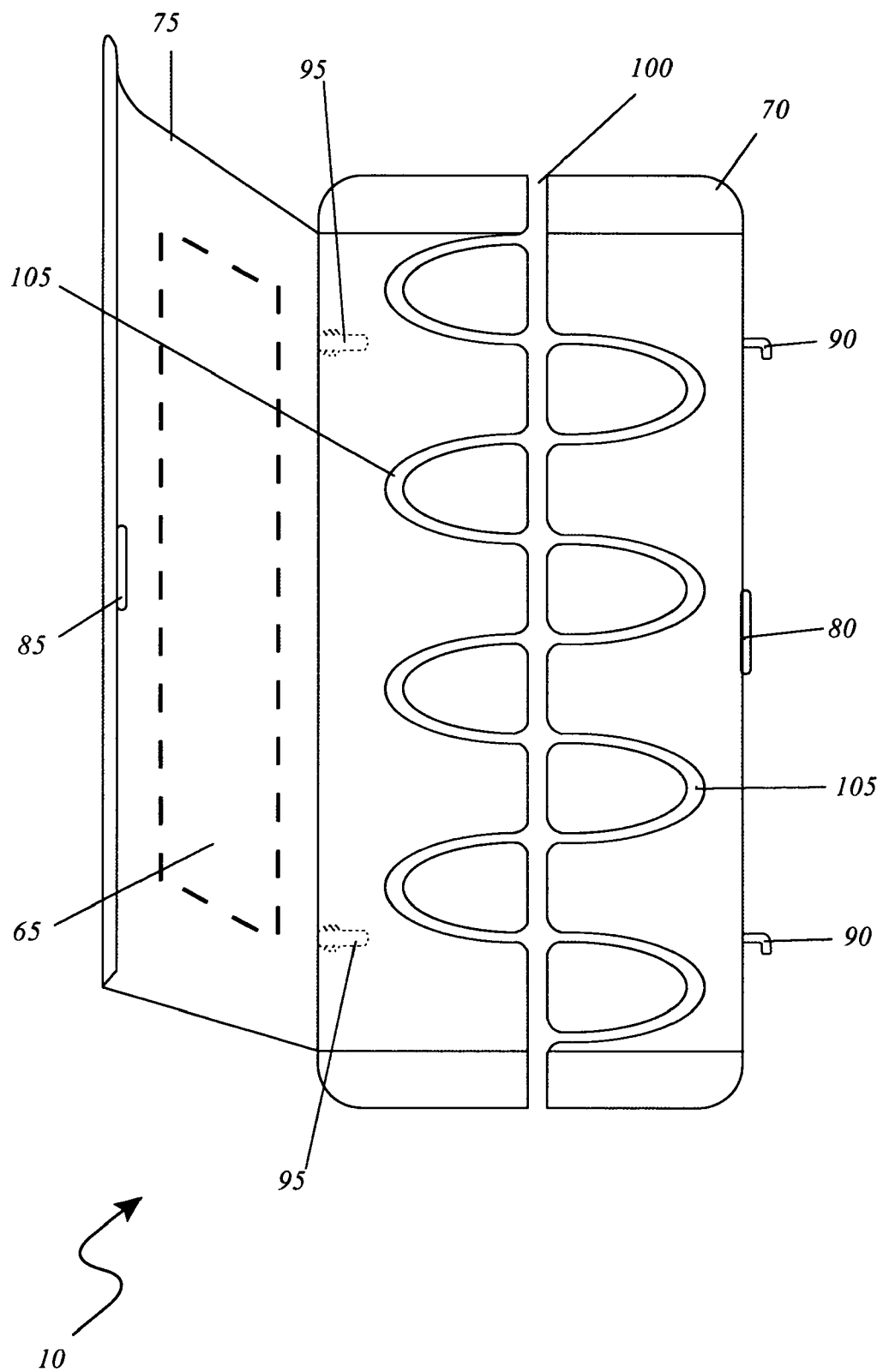

Referring next to FIG. 2, a front view of the apparatus to contain excessive lengths of medical tubing and cabling 10 shown in an open and unutilized state is depicted. The apparatus to contain excessive lengths of medical tubing and cabling 10 consists of a lower base assembly 70 with a captive cover 75 arranged in a clamshell design. The lower base assembly 70 and captive cover 75 are envisioned to be made of a pliable plastic that will somewhat bend and conform as external pressure is applied. This in lieu of a hard plastic construction. The lower base assembly 70 and the captive cover 75 are envisioned to be produced as one integral component in an injection and/or blow molding process. However, those familiar in the art will realize that other methods of production and material of manufacture can be utilized, and as such, should not be interpreted as a limiting factor of the present invention. The lower base assembly 70 is provided with a clasp engagement means 80 and the captive cover 75 is provided with a clasp 85. The clasp engagement means 80 and the clasp 85 work together to hold the apparatus to contain excessive lengths of medical tubing and cabling 10 closed and allow the opening of the apparatus to contain excessive lengths of medical tubing and cabling 10 with simple finger pressure in a well-known process. On one side of the apparatus to contain excessive lengths of medical tubing and cabling 10 a series of multiple arrangement connection appendages 90 is located. Said multiple arrangement connection appendages 90 work in conjunction with a matching set of multiple arrangement connection receptacles 95, here depicted by hidden lines for purposes of illustration, to allow the connection of multiple apparatus to contain excessive lengths of medical tubing and cabling 10 into a ganged arrangement. Said ganged arrangement would be used on those patient 15 (as shown in FIG. 1) requiring more than one intravenous tubing 40 (as shown in FIG. 1) or the use of other linear based care mechanisms such as monitoring cables, tubes, vacuum lines, oxygen lines, and the like. The multiple arrangement connection appendages 90 and the multiple arrangement connection receptacles 95 allow the apparatus to contain excessive lengths of medical tubing and cabling 10 to be snapped together and apart by hand requiring the use of no tools. The label writing area 65 is shown in hidden lines as well to indicate its placement on the front of the captive cover 75. Finally, located in the interior of the lower base assembly 70, is a straight captive path 100 and an "S"-shaped captive path 105. Further description of the use and functionality of the straight captive path 100 and "S"-shaped captive path 105 will be provided herein below.

Figure 3:
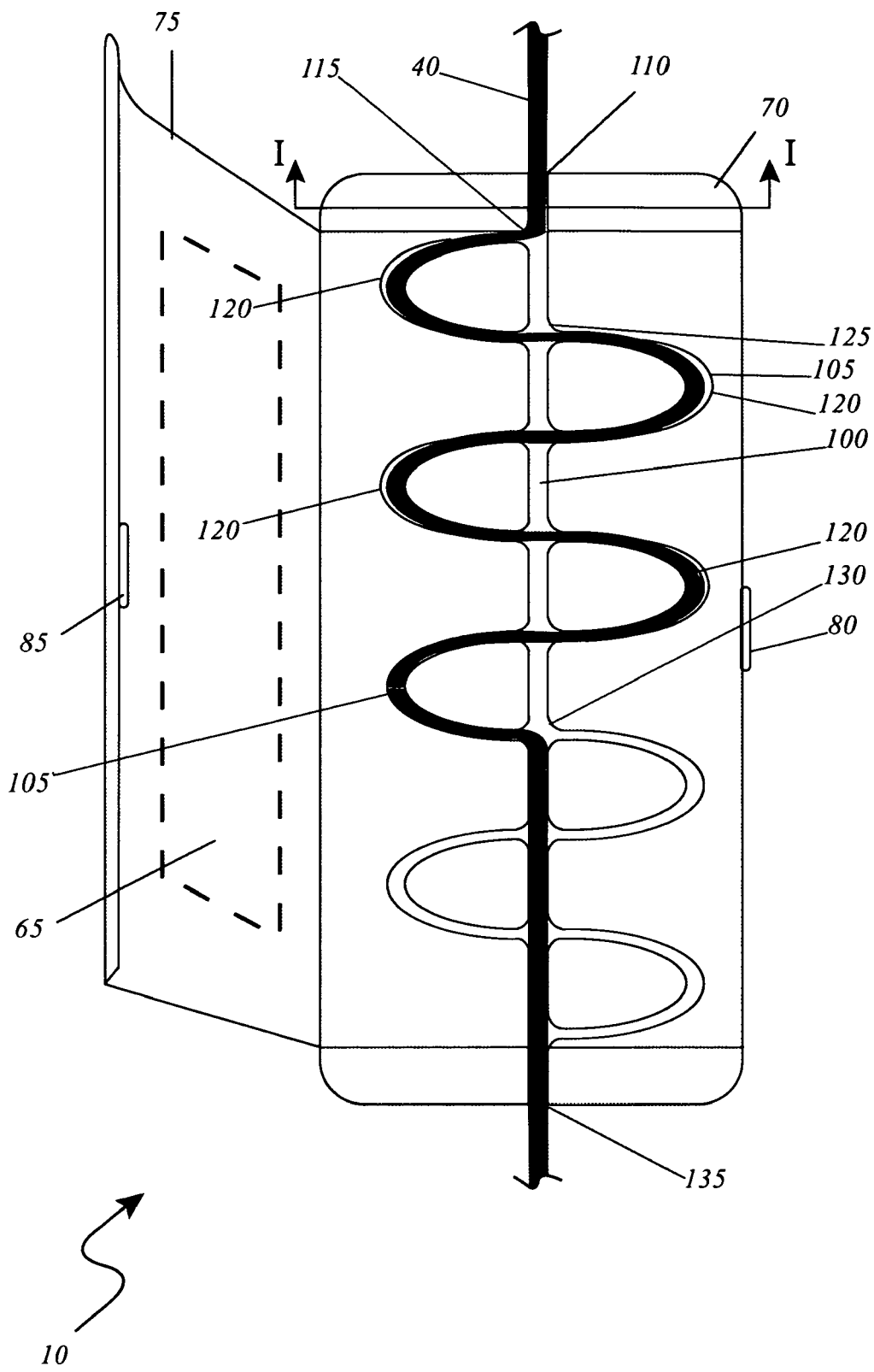

Referring now to FIG. 3, a front view of the apparatus to contain excessive lengths of medical tubing and cabling 10 shown in an open and utilized state is shown. In this FIG., a length of a linear based care mechanism, here depicted as intravenous tubing 40 is installed in the straight captive path 100 and "S"-shaped captive path 105 of the lower base assembly 70 on the apparatus to contain excessive lengths of medical tubing and cabling 10. The intravenous tubing 40 enters from the top of the apparatus to contain excessive lengths of medical tubing and cabling 10 at a entrance opening 110 and is placed over the straight captive path 100 and pushed in using ones finger and gentle pressure. The intravenous tubing 40 is then routed downward towards the bottom of the apparatus to contain excessive lengths of medical tubing and cabling 10. Upon reaching a first intersection point 115 of the straight captive path 100 and the "S"-shaped captive path 105, the user would route the intravenous tubing 40 along a "U"-shaped captive path segment 120 until reaching a second intersection point 125. The user would continue along the "S"-shaped captive path 105 in a straight manner until reaching and occupying another "U"-shaped captive path segment 120. Such action would continue along the various sequential "U"-shaped captive path segment 120 until adequate slack in the intravenous tubing 40 has been absorbed. At this point the user will be near a 'nth' intersection point 130 whereupon the intravenous tubing 40 would then change direction and be routed along the straight captive path 100 and out of the bottom of the apparatus to contain excessive lengths of medical tubing and cabling 10 at an exit opening 135. At this point the user can close the captive cover 75 and secure it with the use of the clasp engagement means 80 and clasp 85 to ensure the intravenous tubing 40 remains captive along its entire length contained within the apparatus to contain excessive lengths of medical tubing and cabling 10.

Figure 4:
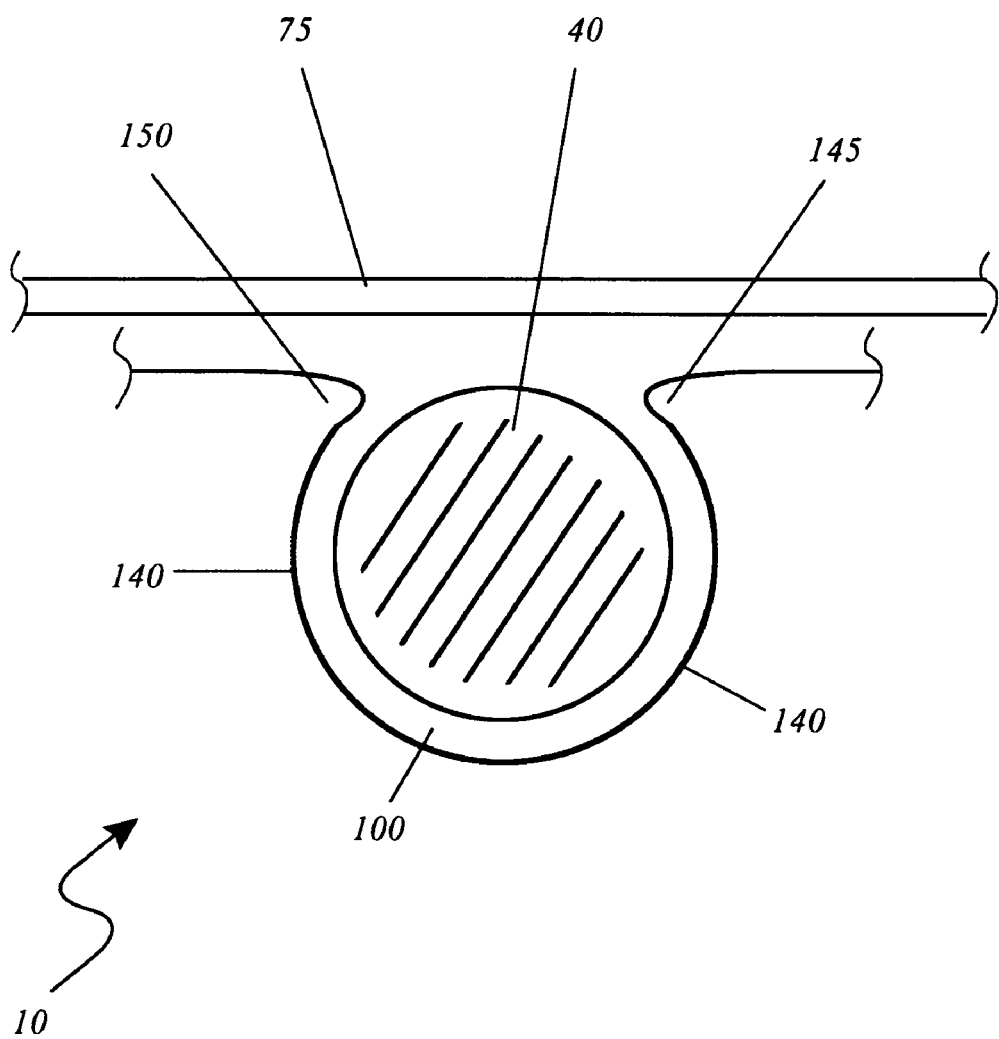

Referring now to FIG. 4, a sectional view of the apparatus to contain excessive lengths of medical tubing and cabling 10 taken along a line I-I as seen in FIG. 3 with the captive cover 75 in a closed position is depicted. This figure clearly depicts the intravenous tubing 40 contained within the straight captive path 100. The intravenous tubing 40 is held in place by a friction fit of the intravenous tubing 40 within a sidewall structure 140 of the straight captive path 100. Retention is further aided with the use of a right side nub appendage 145 and a left side nub appendage 150. The right side nub appendage 145 and the left side nub appendage 150 cause the intravenous tubing 40 or other linear based medical care mechanism to slightly deform in an oblong manner as it passes said right side nub appendage 145 and left side nub appendage 150. Upon passing, the intravenous tubing 40 then expands to refill the complete void of the straight captive path 100. To further aid in the retention of the intravenous tubing 40, the captive cover 75 provides additional retention means.

Figure 5:
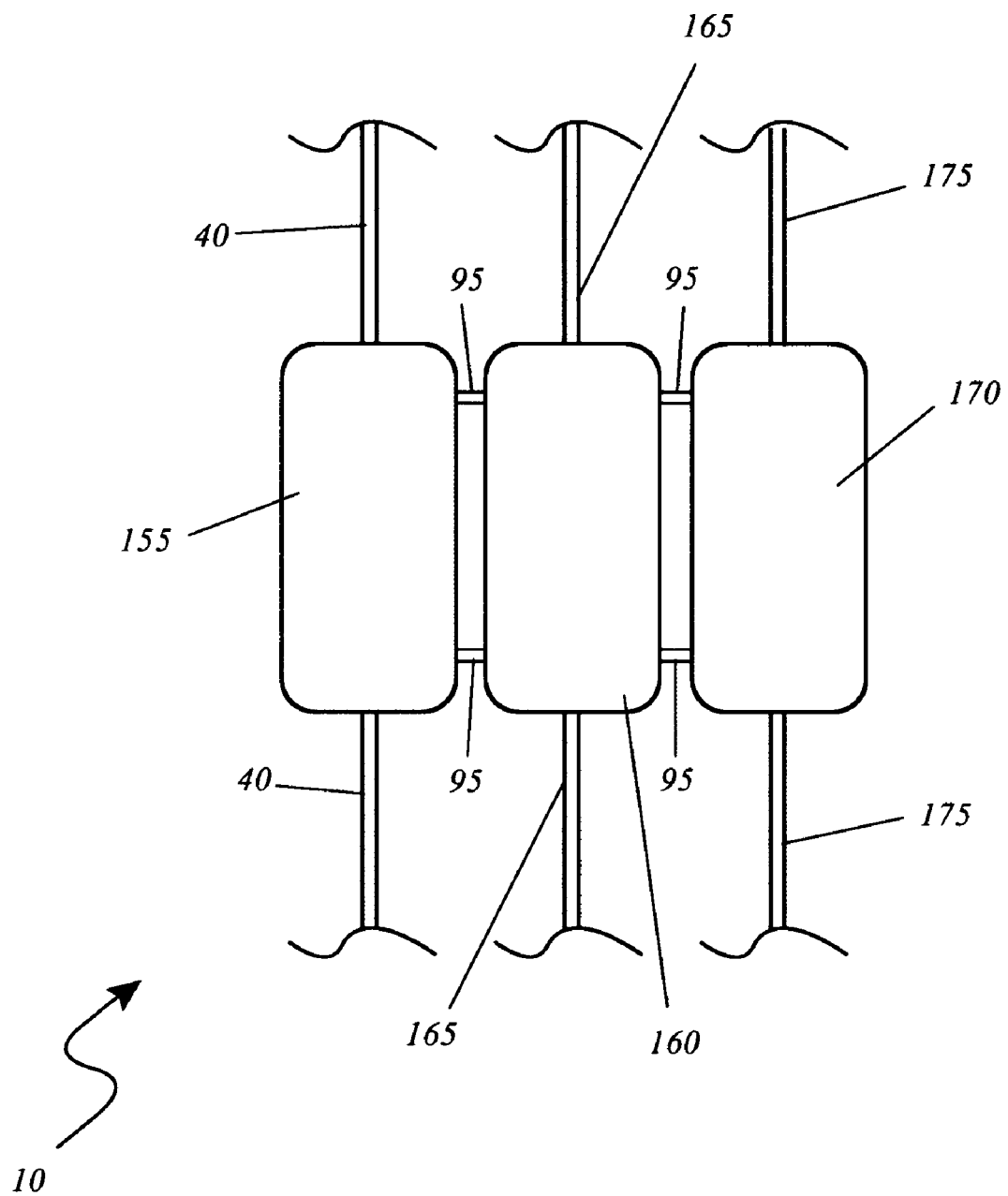

Referring finally to FIG. 5, an isometric view of the apparatus to contain excessive lengths of medical tubing and cabling 10 shown in a multi-ganged arrangement is disclosed. This figure clearly shows the multi-ganged arrangement capability of the apparatus to contain excessive lengths of medical tubing and cabling 10. In this figure a first multi-ganged arrangement module 155 contains excess amounts of intravenous tubing 40, in a manner aforementioned described in FIG. 3. A second multi-ganged arrangement module 160 is attached to the first multi-ganged arrangement module 155 using the multiple arrangement connection appendages 90 (as shown on FIG. 1) on the first multi-ganged arrangement module 155 in conjunction with the multiple arrangement connection receptacles 95 on the second multi-ganged arrangement module 160. The second multi-ganged arrangement module 160 is portrayed as containing an oxygen line 165. In a similar mounting arrangement, a third multi-ganged arrangement module 170 is connected to the second multi-ganged arrangement module 160. The third multi-ganged arrangement module 170 is portrayed as containing an electrical monitoring cable 175. Said configurations are unlimited with regards to numbers of apparatus to contain excessive lengths of medical tubing and cabling 10 that are interconnected as well as the linear based medical care mechanisms contained within.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. To utilize the apparatus to contain excessive lengths of medical tubing and cabling 10, the nurse, doctor, or care provider would place the necessary linear based medical care device following normally accepted practices and procedures. It is envisioned that virtually any liner based medical care mechanism could be contained within the apparatus to contain excessive lengths of medical tubing and cabling 10. After placement is complete, the nurse, doctor or care provider is ready to place the apparatus to contain excessive lengths of medical tubing and cabling 10 in its location.

After approximating the amount of excess linear based medical care device available, herewith referred to as the intravenous tubing 40 for purposes of simplicity, to be eliminated, the care provider would open the captive cover 75 on the apparatus to contain excessive lengths of medical tubing and cabling 10 by use of the clasp engagement means 80 and clasp 85. A length of the intravenous tubing 40 is installed in the straight captive path 100 and "S"-shaped captive path 105 of the lower base assembly 70 on the apparatus to contain excessive lengths of medical tubing and cabling 10. The intravenous tubing 40 enters from the top of the apparatus to contain excessive lengths of medical tubing and cabling 10 at the entrance opening 110 and is placed over the straight captive path 100 and pushed in using ones finger and gentle pressure. The intravenous tubing 40 is then routed downward towards the bottom of the apparatus to contain excessive lengths of medical tubing and cabling 10. Upon reaching the first intersection point 115 of the straight captive path 100 and the "S"-shaped captive path 105, the user would route the intravenous tubing 40 along the "U"-shaped captive path segment 120 until reaching the second intersection point 125. The user would continue along the "S"-shaped captive path 105 in a straight manner until reaching and occupying another "U"-shaped captive path segment 120. Such action would continue along the various sequential "U"-shaped captive path segment 120 until adequate slack in the intravenous tubing 40 has been absorbed. At this point the user will be near the "nth" intersection point 130 whereupon the intravenous tubing 40 would then change direction and be routed along the straight captive path 100 and out of the bottom of the apparatus to contain excessive lengths of medical tubing and cabling 10 at an exit opening 135. At this point the user can close the captive cover 75 and secure it with the use of the clasp engagement means 80 and clasp 85 to ensure the intravenous tubing 40 remains captive along its entire length contained within the apparatus to contain excessive lengths of medical tubing and cabling 10. The care provider can secure the apparatus to contain excessive lengths of medical tubing and cabling 10 to a nearby object with the elastic strap 45 and fastening means 50 if desired. Finally, the care provider can write any desired information on the label writing area 65 provided on the captive cover 75 of the apparatus to contain excessive lengths of medical tubing and cabling 10.

To remove the intravenous tubing 40 from the apparatus to contain excessive lengths of medical tubing and cabling 10, the care provider would hold the apparatus to contain excessive lengths of medical tubing and cabling 10 in one hand and then pull the cable out with the other, thus allowing the apparatus to contain excessive lengths of medical tubing and cabling 10 to be reused in a repeating manner.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. An apparatus for containing excessive lengths of linear based care mechanism, comprising:
    a lower base assembly having:
        an entrance opening;
        an exit opening; and,
        a plurality of grooves forming a captive path, the captive path leading from the entrance opening to meet the exit opening, such that, the captive path receives and contains the excessive lengths of linear based care mechanism;
    a captive cover hinged at one end portion to the lower base assembly, such that, the captive cover is capable of covering the excessive lengths of linear based care mechanism, contained in the captive path of the lower base assembly;
    a fastening means for securely fastening said apparatus thereto a local support; and,
    at least one multiple arrangement connection appendage and at least one multiple arrangement connection receptacle, the multiple arrangement connection appendages capable of snapping with the multiple arrangement connection receptacle disposed on another apparatus, thereby configuring a ganged arrangement of a plurality of the apparatus.

2. The apparatus of claim 1, further comprising a clasp disposed on the captive cover capable of engaging with a clasp engagement means disposed on the lower base assembly.

3. The apparatus of claim 1, further comprising a label writing area disposed on a front surface of the captive cover, the label writing area allowing care providers to indicate functionality of the contained linear based care mechanism.

4. The apparatus of claim 1, wherein the captive path comprises a straight captive path and a curved captive path, arranged in a manner, such that, the linear based care mechanism entering the apparatus through the entrance opening, follows a combination of the straight captive path and the curved captive path and leaves the apparatus through the exit opening.

5. The apparatus of claim 4, wherein the curved captive path is an "S"-shaped captive path.

6. The apparatus of claim 1, wherein the linear based care mechanism is selected from the group consisting of vacuum lines, feeding tubes, drain lines, oxygen lines, and electrical monitoring cables.

7. The apparatus of claim 1, wherein the lower base assembly and the captive cover are made of pliable plastic.

8. The apparatus of claim 1, wherein the linear based care mechanism is held in place by a friction fit of the linear based care mechanism within a sidewall structure of the captive path and the sidewall structure comprises a right side nub appendage and a left side nub appendage, capable of causing the linear based care mechanism to slightly deform in an oblong manner, thereby providing retention to the linear based care mechanism.

9. An apparatus for containing excessive lengths of linear based care mechanism, comprising:
    a lower base assembly having:
        an entrance opening disposed at a top of the lower base assembly;
        an exit opening disposed at a bottom of the lower base assembly;
        a plurality of grooves forming a straight captive path and a "S"-shaped captive path, arranged in a manner, such that, a combination of the straight captive path and the "S"-shaped captive path is capable of receiving and containing the excessive lengths of the linear based care mechanism; and, a captive cover hinged at one end portion to the lower base assembly, the captive cover having a clasp capable of engaging to a clasp engagement means disposed on the lower base assembly, such that, the captive cover is capable of covering the excessive lengths of linear based care mechanism, contained in the combination of the straight captive path and the "S"-shaped captive path of the lower base assembly.

10. The apparatus of claim 9, wherein the linear based care mechanism is selected from the group consisting of vacuum lines, feeding tubes, drain lines, oxygen lines, and electrical monitoring cables.

11. The apparatus of claim 9, further comprising a label writing area disposed on a front surface of the captive cover, the label writing area allowing care providers to indicate functionality of the contained linear based care mechanism.

12. The apparatus of claim 9, further comprising at least one multiple arrangement connection appendage and at least one multiple arrangement connection receptacle, the multiple arrangement connection appendages capable of snapping with the multiple arrangement connection receptacle disposed on another apparatus, thereby configuring a ganged arrangement of a plurality of the apparatus.

13. The apparatus of claim 9, wherein the lower base assembly and the captive cover are made of pliable plastic.

14. The apparatus of claim 9, wherein the linear based care mechanism is held in place by a friction fit of the linear based care mechanism within a sidewall structure of the straight captive path and the "S"-shaped captive path.

15. The apparatus of claim 14, wherein the sidewall structure comprises a right side nub appendage and a left side nub appendage, capable of causing the linear based care mechanism to slightly deform in an oblong manner, thereby providing retention to the linear based care mechanism.

16. A method of using an apparatus for containing excessive lengths of linear based care mechanism having a lower base assembly, and a captive cover hinged to the lower base assembly, comprising:
  inserting the linear based care mechanism at an entrance opening of the lower assembly;
  routing the linear based care mechanism downwardly towards a straight captive path of the lower base assembly, and further along a "S"-shaped captive path of the lower base assembly towards a plurality of intersection points of the straight captive path and 'S' shaped captive path until the linear based mechanism reaches a predetermined intersection point of the plurality of intersection points whereupon the linear based care mechanism changes direction and routed along the straight captive path and out of an exit opening of the lower base assembly; and,
  closing the captive cover by engaging a clasp of the captive cover with a clasp engagement means of the lower base assembly, thereby ensuring the linear based care mechanism remaining captive therewithin.

17. The method of claim 16, wherein the linear based care mechanism, is selected from the group consisting of vacuum lines, feeding tubes, drain lines, oxygen lines, and electrical monitoring cables.

18. The method of claim 16, further comprising connecting a plurality of apparatus forming a ganged arrangement by snapping a multiple arrangement connection appendage of a first apparatus to a multiple arrangement connection receptacle of a second apparatus.

* * * * *